United States Patent [19]

Kurtz et al.

[11] Patent Number: 4,752,287
[45] Date of Patent: Jun. 21, 1988

[54] SYRINGE CHECK VALVE

[75] Inventors: Robert J. Kurtz, New York; Joseph LiCausi, Port Jefferson Station, both of N.Y.

[73] Assignee: BioResearch, Inc., Farmingdale, N.Y.

[21] Appl. No.: 947,802

[22] Filed: Dec. 30, 1986

[51] Int. Cl.$^4$ .............................................. A61M 25/00
[52] U.S. Cl. ...................................... 604/99; 604/256; 251/149.1
[58] Field of Search ............... 251/149.1, 148; 604/99, 604/256

[56] References Cited

U.S. PATENT DOCUMENTS

| 3,138,161 | 6/1964 | Allen | 128/348 |
|---|---|---|---|
| 3,192,949 | 7/1965 | De See | 137/540 |
| 3,352,531 | 11/1967 | Kilmarx | 251/149.6 |
| 3,477,438 | 11/1969 | Allen et al. | 128/349 |
| 3,495,594 | 2/1970 | Swanson | 128/349 |
| 3,577,992 | 5/1971 | Merry | 128/349 |
| 3,601,152 | 8/1971 | Kenworthy | 137/525 |
| 3,831,629 | 8/1974 | Mackal et al. | 137/525 |
| 3,837,381 | 9/1974 | Arroyo | 251/149.1 X |
| 4,143,853 | 3/1979 | Abramson | 251/149.1 |
| 4,205,683 | 6/1980 | O'Neill | 128/348 |
| 4,244,379 | 1/1981 | Smith | 128/766 |
| 4,421,296 | 12/1983 | Stephens | 251/149.7 |
| 4,545,367 | 10/1985 | Tucci | 128/1 R |

FOREIGN PATENT DOCUMENTS 964544  3/1975  Canada .................................. 604/99

Primary Examiner—Dalton L. Truluck
Attorney, Agent, or Firm—Larson and Taylor

[57] ABSTRACT

A syringe check valve for use with a flexible catheter tube. The valve includes a rigid tubular cap and an elastomeric valve member. The valve member is partially inserted into a flexible catheter tube and the rigid cap is slipped over the valve member to maintain the flexible tube on the valve member and to force the valve slot in the valve member closed. The valve is used by inserting the blunt end of a syringe into a tapered cylindrical bore in the valve member which is in communication with the valve slot. The contact of the end of the syringe with the interior walls of the tapered cylindrical bore forces open the valve slot and allows passage of fluid through the valve.

5 Claims, 3 Drawing Sheets

SYRINGE CHECK VALVE

FIELD OF THE INVENTION

The invention relates to syringe check valves for use in combination with flexible catheters and more specifically with a Foley catheter having an inflatable balloon at the distal end.

BACKGROUND OF THE INVENTION

It is frequently desirable to provide a valve for use with a Foley catheter which valve may be opened or closed at will simply by inserting the blunt end of a syringe without a needle into the valve. This is particularly useful in connection with a Foley catheter wherein it is necessary to inflate and deflate the catheter balloon expeditiously.

An example of a prior art type of valve is shown in U.S. Pat. No. 3,477,438 (Allen et al). This particular valve includes a plug having an integral normally closed self-sealing apertured portion having a passage therethrough which is formed by puncturing the tube end, and a tension member which fits over the plug and inside the catheter tube. In operation, a syringe is inserted into the passage in the apertured portion and comes into contact with the normally closed end of the plug thereby pushing on the end of the plug to force open the aperture. The valve member is adhesively fixed in the catheter tube and the assembly of the three parts including the formation of the slit, glueing of the inner part in the outer parts and fixing the two parts within the catheter tube is difficult, time consuming and is always expensive.

Another example of a syringe actuated valve is U.S. Pat. No. 3,495,594 (Swanson). This valve includes a housing, a resilient plug and a retaining member. This valve requires assembly prior to connection to the catheter. In addition, a needle is necessary to puncture the solid plug material and thereby open the valve. This valve cannot be opened without inserting a needle therein.

U.S. Pat. No. 3,837,381 (Arroyo) is a three piece valve device for use with catheters. The device includes a body, a hollow tubular member cover, and a ring member. To assemble this valve the ring member is slipped over a flexible tube, the body is inserted into the flexible tube, the tubular cover is placed over the body and flexible tube, and finally the ring member is forced between the tubular cover and the flexible tube to provide additional support to the valve. This valve relies on the resilience of the flexible tube to retain the valve channel in the closed position. This is not highly reliable since the size or resiliency of catheter tubes may vary. Also, this valve cannot be opened without insertion of a syringe.

Therefore, there is a need in the art for a catheter valve which overcomes the aforementioned disadvantages.

It is the primary object of the present invention to provide a syringe-actuated valve member for a Foley catheter which is formed of two parts and which requires no precutting or glueing to secure the valve in place and which is effective in preventing leakage between the valve and catheter.

It is another object of the present invention to provide an inexpensive syringe check valve for a catheter which is easy to use.

It is a further object of the present invention to provide a syringe check valve that requires little or no assembly.

These and other objects of the present invention will be apparent to one of ordinary skill in the art from the summary and detailed description which follow.

SUMMARY OF THE INVENTION

The present invention relates to a syringe check valve for use with flexible catheters. The valve includes two parts, an elastomeric valve member and a rigid hollow tubular cap. The valve member is made as a completely molded one piece unit havng an elongate portion with an elongate bore therein and a base portion. The elongate portion is inserted into the flexible catheter tube such that the elongate bore communicates with the catheter tube. The base portion remains outside the flexible tube. The base portion has a tapered cylindrical bore extending axially into it. The smaller end of the cylindrical bore communicates with a valve slot which also extends axially through the base portion and communicates with the elongate bore. The base portion further includes a pair of shoulders which extend radially outward from the valve slot in opposing relationship.

The rigid hollow tubular cap has a first end that fits over the shoulders of the valve member and exerts radial pressure on the shoulders to close the valve slot. The tubular cap also has a second tapered end which fits over the catheter tube and the elongate portion of the valve member to maintain the catheter tube pressed between the tapered end of the cap and the elongate portion of the valve member. The valve slot is opened at will by sliding the cap off the valve member or by introducing the blunt end of a syringe into the tapered cylindrical bore to force open the valve slot.

In a preferred embodiment the elongate portion of the valve member is tapered and includes a pair of annular flanges to aid in holding the flexible catheter tube and the cap on the elongate portion. Also, in a preferred embodiment the cap includes an internal annular flange to prevent the tapered portion of the cap from sliding over the shoulders of the valve member.

Other objects and many of the attendant advantages of the present invention will become more readily apparent upon consideration of the following detailed specification in connection with the accompanying drawings wherein:

DETAILED DESCRIPTION OF THE PREFERRED EMBODIMENT

Figure 1:
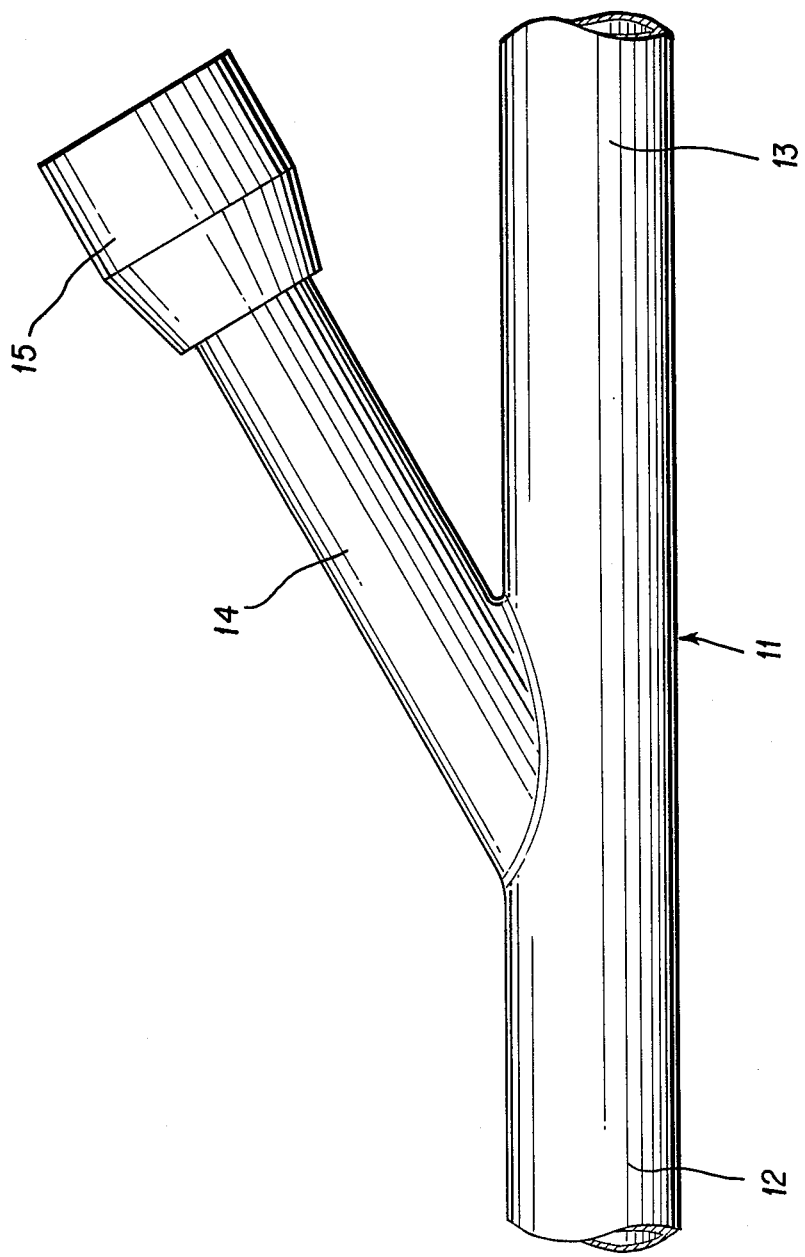
FIG. 1 is a front elevation of a catheter showing the valve means of the present invention on the side arm of the catheter.

The catheter of the present invention is of the type which includes a flexible tube 11 provided with a passage therethrough. The catheter includes a distal end 12 and a proximal end 13. At the proximal end 13 there is attached a side-arm 14 to the flexible tube 11. At the distal end there is provided a balloon (not shown) and a separate inflation passage (not shown) extends from the balloon to the side arm 14 passageway. The side-arm 14 has an open, free end to which the syringe check valve 15 according to the present invention is attached.

The check valve 15 is composed of an elastomeric valve member 16 formed of rubber or like material and a hollow tubular cap 17 formed from a rigid plastic material.

Figure 4:
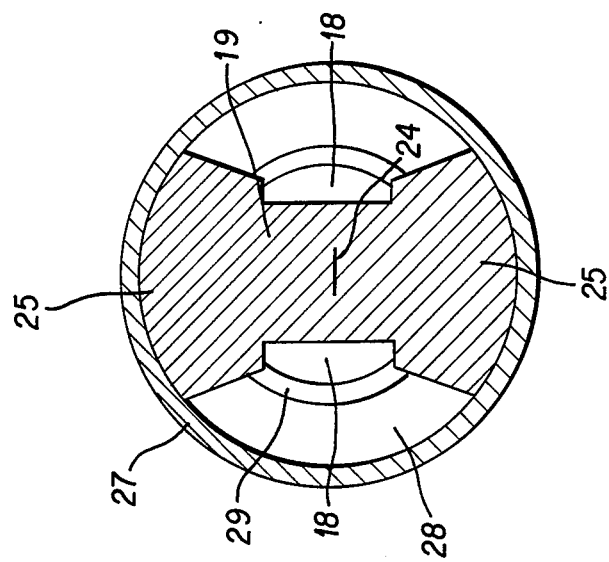
FIG. 4 is a cross-sectional view taken along the line A—A in FIG. 2 of the valve body together with the cap thereon.
Figure 3:
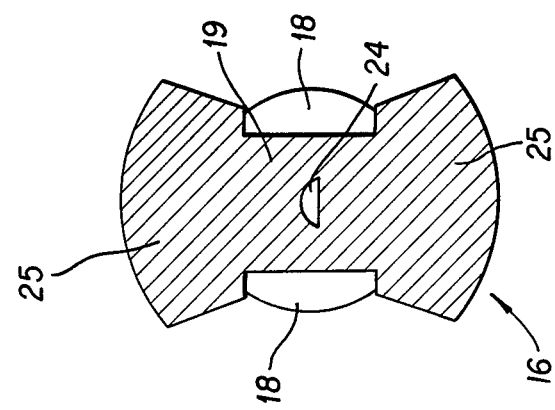
FIG. 3 is a cross-sectional view taken along the line A—A in FIG. 2 of the valve body without the cap thereon.

The elastomeric valve member 16 includes an elongate portion 18 and a base portion 19. The elongate portion 18 has an elongate bore 20 therein. The elongate portion 18 also includes a first annular flange 21 and a second annular flange 22 longitudinally spaced therefrom. The base portion 19 is provided with a tapered bore 23 extending axially into it and communicating with a valve slot 24 which extends axially centrally of the base 19 into communication with bore 20. The valve slot is formed with a straight side cut approximately 0.09 inch long and a semicircular side cut along a 0.30 inch radius. As shown in FIG. 3 and 4 the base portion 19 has a pair of shoulders 25 extending radially outward from the valve slot 24 in opposed relation. Each shoulder extends around approximately 40° of the periphery of the valve member.

The rigid tubular cap 17 has a first end 27 and a second tapered end 28. The tubular cap 17 has an internal annular flange 29 located at the point in the tubular cap 17 wherein the tubular cap 17 begins to taper.

To attach the valve 15 to the flexible tube 11 of a catheter, which is preferably a Foley catheter, the tubular cap 17 is placed over the flexible tube 11 and slipped a considerable distance down the flexible tube 11 until the end of tube 11 extends well beyond the end 27 of the cap. The elongate portion 18 of the elastomeric valve member 16 is then inserted into the flexible tube 11 until the end of the flexible tube 11 contacts the base portion 19 of the valve member 16. At this point the valve slot 24 is in the open position. The tubular cap 17 is then pulled over the flexible tube 11 and the elongate portion 11 until the internal annular flange 29 contacts the shoulders 25 of the base portion 19. The valve member 16 is now ready for use. In this configuration the first end 27 of the tubular cap 17 exerts inward radial pressure on the shoulders 25 of the base portion 19 to force the valve slot 24 closed. The tapered end portion 28 locks the end portion of tube 11 into the flange 21 of the valve member 16 so as to retain the catheter tube 11 in tight sealing engagement with the valve member without the need for any glueing. The pressure exerted on the base portion 19 is only exerted along a line extending perpendicular to the straight side cut of the valve slot 24. This provides for a minimum application of pressure to close the valve slot 24 since substantially all of the applied pressure is exerted in the optimum direction for the closing of the valve slot 24. The application of inward radial pressure to the base portion 19 in a direction parallel to the straight side cut of valve slot 24 would only serve to force the valve slot 24 open and would work against the force applied by the shoulder 25. The present invention only applies force to the base portion 19 in the directions which cause the base portion 19 to be squeezed to close the valve slot 24. This, in turn, allows the present invention to employ a slightly more rigid valve member 16 which is more readily inserted into the flexible tube 11.

The second tapered end 28 of the tubular cap 17 squeezes the flexible tube 11 against the first annular flange 22 of the elongate portion 18 to aid in maintaining the flexible tube 11 on the elongate portion 18. In addition, the second annular flange 21 of the elongate portion 18 engages the end of the second tapered end 28 of the tubular cap 17 to aid in maintaining the tubular cap 17 in position on the valve member 16 and flexible tube 11.

Figure 2:
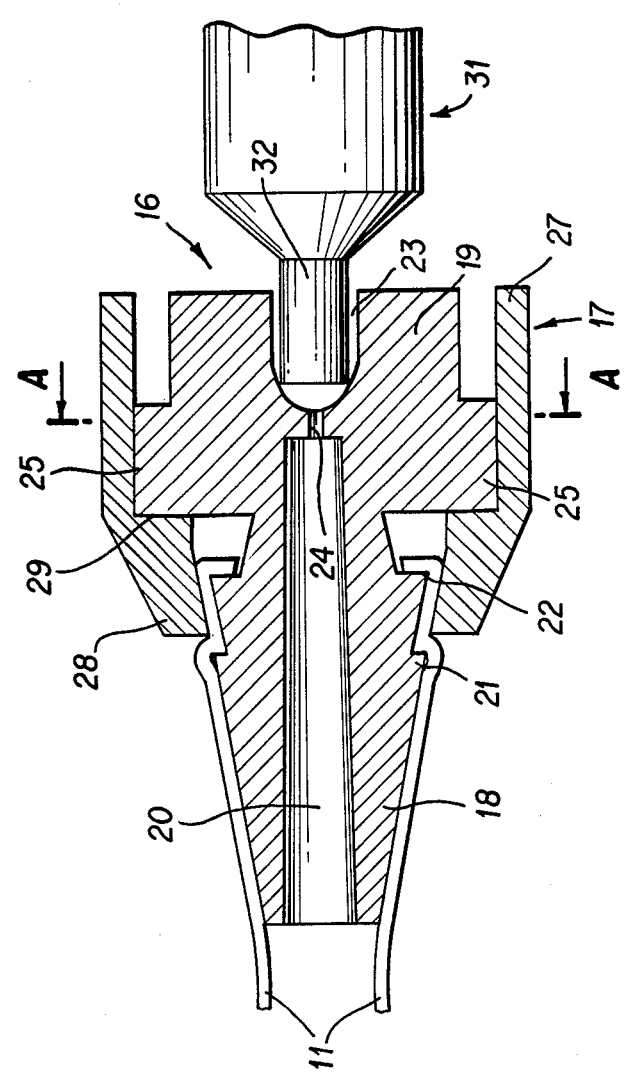
FIG. 2 is a cross-section taken through the valve and side-arm of the catheter shown in FIG. 1 showing a syringe inserted in the valve.

In operation the user takes a syringe 31 without a needle thereon and introduces the syringe tip 32 into the tapered cylindrical bore 23 of the valve 17 until the end of the syringe tip 32 engages the inner surface of the tapered cylindrical bore 23. This contact between the syringe tip 32 and the cylindrical bore 23 exerts outward radial pressure on the base portion 19 and thereby forces the valve slot 24 into the open position as shown in FIG. 2. The user may then inject or withdraw fluid through the open valve slot 24 to inflate or deflate the balloon at the distal end of the catheter.

The flexible tube 11 is preferably fabricated from rubber. The rigid tubular cap 17 is preferably plastic and the valve member 16 is an elastomeric material having a durometer range from 10 to 65. The durometer range is important to the attainment of the optimum operation of the valve 15.

The above description has been made in relation to a specific embodiment of the present invention. It is to be understood by those skilled in the art that numerous changes may be made without departing from the spirit of the invention and that the scope of this invention is to be determined by the claims appended hereto.

What is claimed is:

1. A syringe check valve for flexible catheters comprising:
   a flexible catherer tube,
   an elastomeric valve member having a base portion and an elongate portion with a bore therein, said elongate portion being disposed in an end of said catheter tube, said base portion being disposed adjacent the end of said tube said base portion having a tapered cylindrical bore extending axially into the outer end face of the base portion, the smaller end of the bore having a valve slot therein extending axially through said base portion and communicating with said elongate bore, said valve slot comprising a generally elongated slit with at least one generally straight side edge in said base portion, means for applying opposing presure on both sides of the slit and prependicular to the generally straight side edge of said slit to close said slit, said means including a pair of shoulders on said base portion extending radially outward from said valve slot in opposing relationship, said shoulders extending only partially around the periphery of the base portion so as to apply pressure only in a direction to maintain said slit closed, and a rigid hollow tubular cap having a first end disposed over and exerting inward radial pressure on said shoulders to close said valve slot and a second, tapered end disposed on the outer surface of said catherer tube to maintain said catheter tube on said elongate portion, said valve slot adapted to be opened by the introduction of a syringe tip into said tapered cylinderical bore.

2. A syringe check valve as claimed in claim 1 wherein said valve slot is elongated in a direction orthogonal to both the direction of fluid flow and the direction of extension of said shoulders.

3. A syringe check valve as claimed in claim 1 wherein said elongate portion of said valve member further has an annular flange to maintain said catheter tube on said elongate portion of said valve member.

4. A syringe check valve as claimed in claim 3 wherein said elongate portion of said valve member further includes a second annular flange adapted to engage said second tapered end of said cap to maintain said cap on said valve member.

5. A syringe check valve as claimed in claim 4 wherein said cap further includes an internal annular flange adapted to contact said shoulders whereby said cap is retained in locked position on said valve member by engagement of said internal annular flange of the cap with said shoulders of the valve member and engagement of said second tatpered end of the cap with said second annular flange of the valve member.

* * * * *